Figure 1:
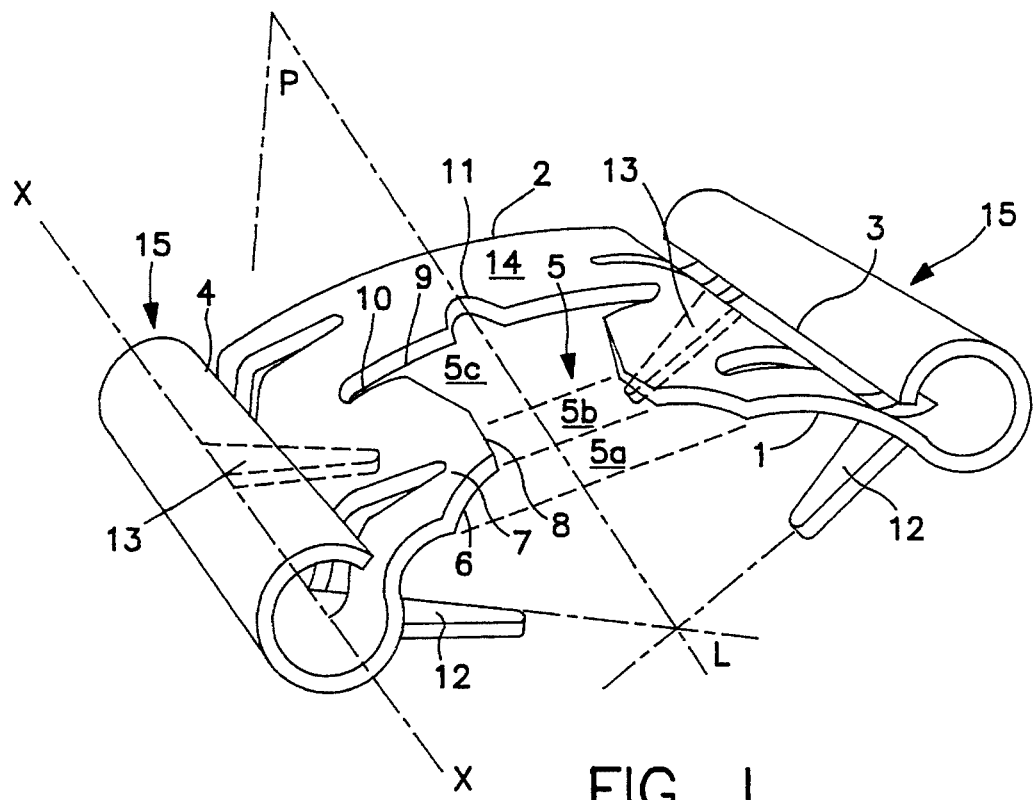

United States Patent [19]
Forster et al.

[11] Patent Number: 5,470,321
[45] Date of Patent: Nov. 28, 1995

[54] DEVICE FOR ATTACHING A FLEXIBLE TUBE TO A PATIENT'S SKIN

[75] Inventors: Michel Ch. Forster, Le Puits, 26760 Beamount-les-Valence; François H. Guillemin, Villers-les-Nancy; Dominique H. Lignon, Vandoeuvre-les-Nancy, all of France

[73] Assignee: Michel Ch. Forster, Beaumont-les-Valence, France

[21] Appl. No.: 318,761

[22] PCT Filed: Feb. 25, 1993

[86] PCT No.: PCT/FR93/00189

§ 371 Date: Oct. 14, 1994

§ 102(e) Date: Oct. 14, 1994

[87] PCT Pub. No.: WO93/16751

PCT Pub. Date: Sep. 2, 1993

[30] Foreign Application Priority Data

Feb. 28, 1992 [FR] France ................... 92 02345

[51] Int. Cl.⁶ ..................................... A61M 25/02
[52] U.S. Cl. .................. 604/174; 128/DIG. 26; 604/178
[58] Field of Search ................... 604/174, 175, 604/177, 179, 180, 178, 176; 128/DIG. 26

[56] References Cited

U.S. PATENT DOCUMENTS

| 3,682,180 | 8/1972 | McFarlane | 604/174 |
| 4,516,968 | 5/1985 | Marshall et al. | 604/174 |
| 4,579,120 | 4/1986 | MacGregor | 604/174 |
| 4,699,616 | 10/1987 | Nowak et al. | 604/180 |
| 4,856,504 | 8/1989 | Yamamoto et al. | 604/180 |
| 5,057,084 | 10/1991 | Ensmwger et al. | 604/175 |
| 5,352,211 | 10/1994 | Merskelly | 604/180 |

*Primary Examiner*—Paul J. Hirsch
*Attorney, Agent, or Firm*—Young & Thompson

[57] ABSTRACT

A device consisting of a metal component which can pass from an "open" position to a "closed" position during use, and has a slot with an insertion channel for receiving a flexible tube (16) near the point where it emerges from a frangible material (17). Said component has first and second fasteners (8,12,13 respectively) which are inoperative when the component is in the open position, and respectively engage said tube (16) and said frangible material (17) when the component is folded into its closed position.

11 Claims, 2 Drawing Sheets

DEVICE FOR ATTACHING A FLEXIBLE TUBE TO A PATIENT'S SKIN

Device for attaching a flexible tube to a pierceable material, in particular a drain to a patient's skin.

The present invention relates to a device for attaching a flexible tube to a pierceable material from which it protrudes, said device having an application in various fields such as horticulture or surgery.

In horticulture, for example, the immobilizing of small watering hoses, called sprinklers, installed on a main hose which is made of rubber and acts as a feed hose, is not satisfactory: the sprinkler is introduced by force into an orifice which is of a diameter smaller than its own and which is formed in the wall of the feed hose, and the connection is ensured only by the compression action exerted by the feed hose on the sprinkler which has been introduced. Consequently, the sprinkler can easily been torn out by accidental pulling.

In surgery it is common practice to position one or more drains in the operation site at the end of a surgical intervention, which drains are intended to remove body fluids and protrude from the body either from intact skin or at the edge of the surgical wound. These drains are removed only after several days of convalescence on the part of the patient, and it is important that they should be immobilized well and that their presence should not lead to any irritation or infection.

The immobilizing technique generally performed consists in tying a suture thread on the drain and fixing the thread to the patient's skin by means of a stitch.

This procedure has its disadvantages:

the suture thread, even if it is correctly placed, constitutes a short chain which does not prohibit the drain from sliding a few millimeters, with the result that it moves back and forth in the skin or the wound, with an obvious risk of infection;

the securing of the suture thread on the drain is difficult, and it can happen that the thread, if insufficiently tight, will slide along the drain, thus aggravating the disadvantage analyzed hereinabove;

the correct positioning of a drain, in the present state of the art, requires a certain amount of time, and any time saving, however small, in routine procedures is important for efficient management of the operating team.

There is therefore a need for a device which would make it possible to attach a flexible tube, such as a drain or a drip, safely and quickly to a pierceable material such as a patient's skin or another flexible tube, respectively, while preventing any relative movement between them.

This aim is achieved by means of the invention in the sense that it provides an attachment device which consists of a metal component capable of being converted, by bending it about a plane, called the "bending" plane, from an "open" configuration before use to a "closed" configuration during use, said component exhibiting a cutout having an access which opens out on one of the edges of the component, said cutout being adapted to receive said tube in the vicinity of the point where it protrudes from said material, said bending plane being median with respect to said cutout and passing through said access, the component exhibiting first and second attachment means which are inactive when said component is in the open configuration and come into engagement with said tube and said pierceable material, respectively, when the component is converted, by bending, to the closed configuration.

In practice, said first attachment means consist of projections provided on opposite edges of the cutout, and these projections exhibit a lead edge adapted to pinch slightly into the wall of the tube (16) upon bending. The geometry of the projections is such that, after bending, said lead edges are perpendicular to the axis of the tube. This ensures a symmetrical longitudinal immobilization of the tube able to withstand the tensile or compressive stresses to which the tube may be subjected.

The second attachment means consist, for their part, of at least one pair of oblique claws, the points of which converge toward a line belonging to said bending plane, and the claws preferably have a length which is such that, after bending, their point intersects the bending plane, so that the points of a given pair of claws cross each other. If appropriate, it is possible to provide for one of the claws, in a pair of opposite claws, to be longer than the other.

It will be understood that the device according to the invention is simultaneously secured, upon bending, on the tube (the drain) by means of the projections of the cutout, and on the pierceable material (the skin) by the claws penetrating in the manner of clips. A single rigid means thus blocks said tube in position in relation to said material.

More precisely, the cutout of the component provides, from upstream to downstream as viewed in the direction of penetration of the tube in the cutout, a gripping zone which gives access to a receiving zone, said gripping zone being of a size which, before bending of the component, allows said tube access to said receiving zone, and said receiving zone being of a size which is adapted to receive a large part of the section of said tube without exerting any appreciable stress on the latter, while a smaller part of the section of the tube remains engaged in said gripping zone.

The cutout exhibits, upstream of the gripping zone, an access zone which opens out on said edge of the component and whose size diminishes toward the gripping zone, thereby forming a ramp, the gripping zone being defined by a narrowing of the cutout resulting from the presence, on each side of the bending plane, of at least one projection. Downstream of the lead edge, each projection falls away, thus giving the cutout a corresponding widening, thereby creating the receiving zone. The effect of this geometry is that, upon bending, the tube is pushed back toward the base of the cutout and is consequently immobilized transversely.

Preferably, the component is slightly curved, at least in its central part, the center of curvature of the component being situated on the same side of said component as the line of convergence of said claws, so that said curvature determines the direction of bending.

The device according to the invention can be manufactured very economically, as a disposable article, which renders its use entirely compatible with the applications envisaged. Indeed, it advantageously consists of a single part which can be manufactured from a metal strip or band by performing simple cutting, stamping, bending operations etc. which are known per se.

The invention extends in scope to the applications of the device according to the invention which have been mentioned hereinabove, and in particular to attaching a surgical drain to a patient's skin.

Figure 2:
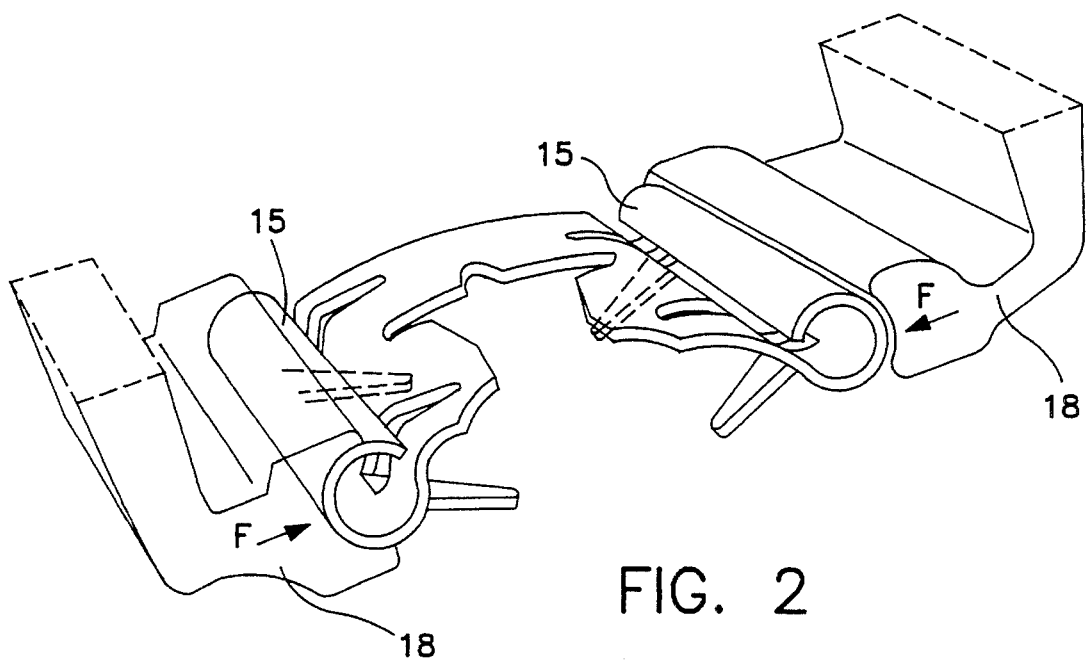
Figure 3:
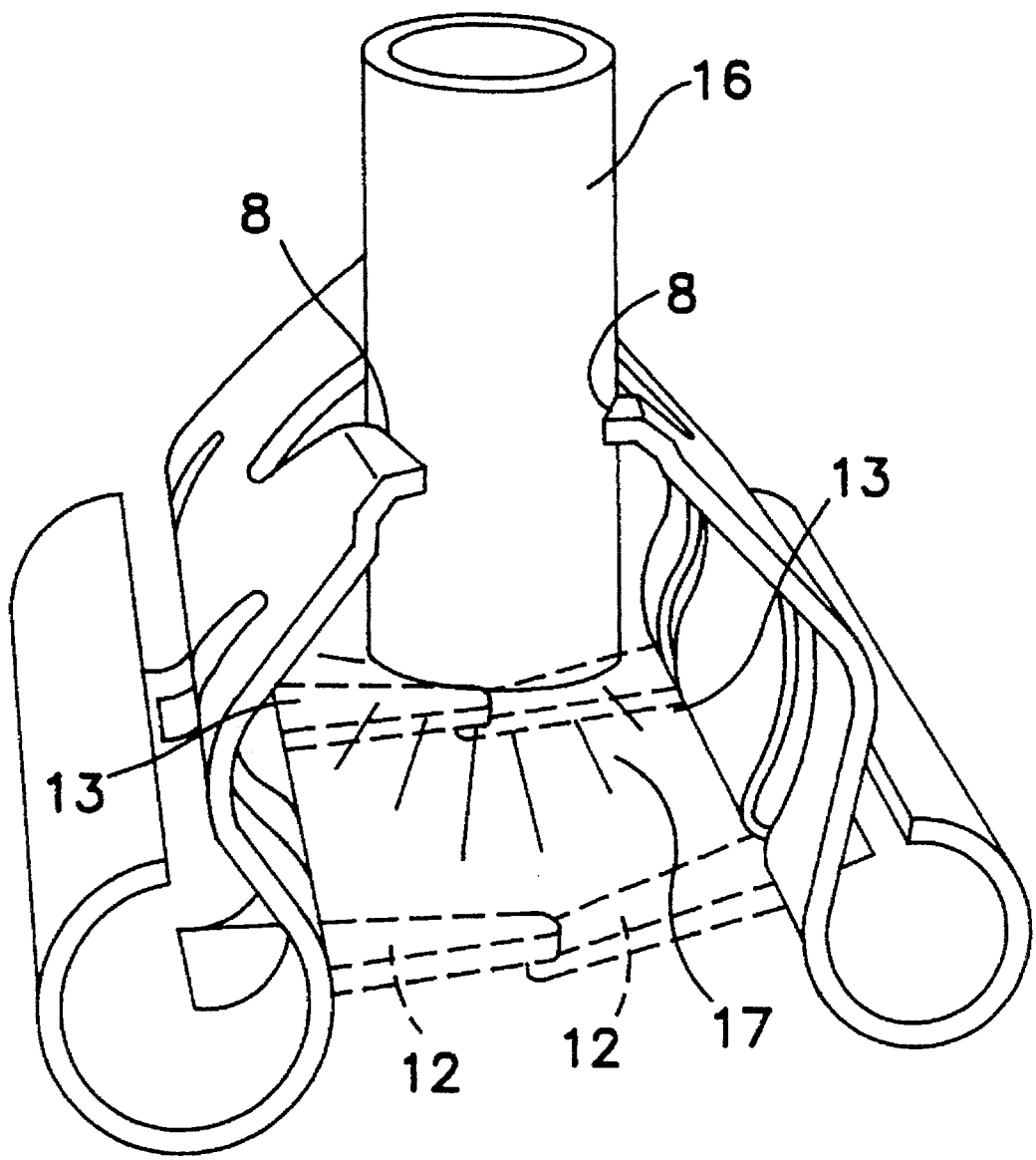

The invention is described hereinbelow, by way of example, with reference to the attached drawings, in which:

FIG. 1 is a perspective view of an embodiment of the device according to the invention, applied for attaching a drain to a patient's skin, said device being represented before use, FIG. 2 is a view similar to FIG. 1, but showing in addition the position of the jaws of a positioning clamp, and FIG. 3 is a perspective view of the device in FIG. 1 during use.

Referring to FIG. 1, a device will be seen which is in one piece and which, before cutting, bending and curving of the metal band or strip from which it is formed, had manifestly the shape of a rectangular blade, the two longitudinal edges of which are designated by 1 and 2, and the two lateral edges of which are designated by 3 and 4. It will also be seen that the component in question presents a plane of symmetry which, in the text which follows, will be called the bending plane P. The component exhibits a cutout 5 which is subdivided from "upstream" to "downstream", that is to say from its open edge toward its base, into three zones, namely an access zone 5a, a gripping zone 5b and a receiving zone 5c. The access zone 5a runs from the longitudinal edge 1 of the component to the gripping zone 5b, and its opposite and curved edges 6 run toward each other, thereby forming an access ramp to the gripping zone 5b. The gripping zone 5b is defined by a narrowing of the cutout resulting from the presence of two projections 7 exhibiting a lead edge 8. Downstream of their lead edge 8, the projections 7 diminish, resulting in a re-widening of the cutout 5, which re-widening creates the receiving zone 5c. Unlike the gripping zone 5b, the receiving zone 5c is limited by a base 9 which defines a slot 10 on each side of the plane P, and also a notch 11 in said plane P. The purpose of these slots and of this notch is to facilitate the deformation of the component during bending, the notch additionally having the specific function of assisting in the correct location of the bending.

The component furthermore comprises two pairs of opposite claws, 12 and 13 respectively. These claws are oblique and are directed toward a convergence line L which belongs to the plane P. The length of the claws 12 and 13 is such that when the device is bent about the plane P, the points of the claws overlap each other (see FIG. 3).

The central part 14 of the component is curved, with its center of curvature situated on the same side of the component as the line L, so that, if the initial curvature is increased by exerting a force in the direction of the arrows F (FIG. 2), the claws of each pair converge on one another.

As can be seen, the lateral ends of the component are rolled inward, each about an axis X—X parallel to the plane P, this strengthening the component and providing lateral grip collars 15.

The use of the device according to the invention is evident from FIG. 3. This shows a drain 16 protruding from the skin 17 of a patient, with the device blocked on the drain 16 and anchored in the skin 17, resulting in the drain being immobilized with respect to the skin. To achieve this result, the drain 16, in the immediate vicinity of the point where it protrudes from the skin 17, has been introduced into the access zone 5a, then the gripping zone 5b, and finally into the receiving zone 5c of the cutout of the device, the latter being in the configuration represented in FIG. 1. The device has then been bent about the plane P by exerting on each collar 15 of the device a clamping force in the direction of the arrows F, either by hand or with the aid of a suitable clamp, the jaws 18 of which are represented in FIG. 2.

This has resulted in:
- on the one hand, in addition to the bending, the lead edges 8 of the projections 7 of the gripping zone 5b being pushed onto the wall of the drain 16, resulting in said drain 16 being pushed back and blocked against the base 9 of the receiving zone 5c and in said lead edges 8 penetrating slightly into the wall of the drain 16, which is thus pinched within the device, and
- on the other hand, the claws of each pair 12, 13 converging toward each other, with their penetrating into the skin 17 until the points of the claws facing each other overlap.

When the drain is to be removed, it suffices to exert, on the collars 15 of the device, forces counter to those indicated by the arrows F, thereby withdrawing the claws 12, 13 from the skin 17, after which the drain and the device are discarded.

The device according to the invention can obviously be manufactured in different sizes and shapes adapted for the application envisaged. If it is intended for surgical application, it will be manufactured from a rustproof, sterilizable and biocompatible material.

Although reference has been made to attaching a tube to a pierceable material, this does not necessarily mean that the claws 12, 13 pierce said material right through, in particular when this is the wall of another tube. It can suffice for the claws to prick this wall. In this case, of course, the points of a pair of opposite claws do not meet upon bending.

We claim:

1. A device for attaching a flexible tube to a pierceable material from which it protrudes, wherein it consists of a metal component capable of being converted, by bending it about a plane, from an "open" configuration before use to a "closed" configuration during use, said component exhibiting a cutout having an access which opens out on one of the edges of the component, said cutout being adapted to receive said tube in the vicinity of the point where it protrudes from said material, said bending plane being median with respect to said cutout and passing through said access, the component exhibiting first and second attachment means which are inactive when said component is in the open configuration and come into engagement with said tube and said pierceable material, respectively, when the component is converted, by bending, to the closed configuration.

2. The device as claimed in claim 1, wherein said first attachment means consist of projections provided on opposite edges of said cutout.

3. The device as claimed in claim 1, wherein said first attachment means consist of projections provided on opposite edges of said cutout, said projections exhibiting a lead edge adapted to pinch slightly into the wall of said tube upon bending, and wherein the geometry of the projections is such that, after bending, said lead edges are perpendicular to the axis of said tube.

4. The device as claimed in claim 1, wherein said second attachment means consist of at least one pair of oblique claws, the points of which converge toward a line belonging to said bending plane.

5. The device as claimed in claim 1, wherein said second attachment means consist of at least one pair of oblique claws, the points of which converge toward a line belonging to said bending plane and the length of which is such that, after bending, their point intersects said bending plane.

6. The device as claimed in claim 1, wherein said cutout provides, from upstream to downstream as viewed in the direction of penetration of said tube in said cutout, a gripping zone which gives access to a receiving zone, said gripping zone being of a size which, before bending of the component, allows said tube access to said receiving zone, and said receiving zone being of a size which is adapted to receive a large part of the section of said tube without exerting any appreciable stress on the tube, while a smaller part of the section of the tube remains engaged in said gripping zone.

7. The device as claimed in claim 1, wherein said cutout provides, from upstream to downstream as viewed in the direction of penetration of said tube in said cutout, a gripping zone which gives access to a receiving zone, said cutout exhibiting, upstream of said gripping zone, an access zone, said gripping zone being of a size which, before bending of the component, allows said tube access to said receiving zone, said receiving zone being of a size which is adapted to receive a large part of the section of said tube without exerting any appreciable stress on the tube, while a smaller part of the section of the tube remains engaged in said gripping zone, said access zone opening out on said edge of the component and being of a size which diminishes toward said gripping zone, thereby forming a ramp, said gripping zone being defined by a narrowing of said cutout resulting from the presence, on each side of said bending plane, of at least one projection.

8. The device as claimed in claim 1, wherein said cutout provides, from upstream to downstream as viewed in the direction of penetration of said tube in the cutout, a gripping zone which gives access to a receiving zone, said cutout exhibiting, upstream of said gripping zone, an access zone, said gripping zone being of a size which, before bending of the component, allows said tube access to said receiving zone, said receiving zone being of a size which is adapted to receive a large part of the section of said tube without exerting any appreciable stress on the tube, while a smaller part of the section of the tube remains engaged in said gripping zone, said access zone opening out on said edge of the component and having a size which diminishes toward said gripping zone, thereby forming a ramp, said gripping zone being defined by a narrowing of said cutout resulting from the presence, on each side of said bending plane, of at least one projection which, downstream of said lead edge falls away, thus giving said cutout a corresponding widening, thereby creating said receiving zone.

9. The device as claimed in claim 1, wherein said second attachment means consist of at least one pair of oblique claws, the points of which converge toward a line belonging to said bending plane and wherein the component is slightly curved, at least in its central part, the center of curvature of the component being situated on the same side of said component as the line of convergence of said claws.

10. The device as claimed in claim 1, wherein it consists of a single part and is made from a metal strip or band by performing simple cutting, stamping, or bending operations.

11. The device as claimed in claim 1, made of a rustproof, sterilizable and biocompatible material for attaching a surgical drain to a patient's skin.

* * * * *